(12) United States Patent
Chatellier

(10) Patent No.: US 9,696,282 B2
(45) Date of Patent: Jul. 4, 2017

(54) METHOD FOR MEASURING ELASTIC PROPERTIES USING ULTRASOUND

(71) Applicant: SNECMA, Paris (FR)

(72) Inventor: Jean-Yves Francois Roger Chatellier, Moissy-Cramayel (FR)

(73) Assignee: SNECMA, Paris (FR)

( * ) Notice: Subject to any disclaimer, the term of this patent is extended or adjusted under 35 U.S.C. 154(b) by 354 days.

(21) Appl. No.: 14/365,188

(22) PCT Filed: Dec. 19, 2012

(86) PCT No.: PCT/FR2012/052980
§ 371 (c)(1),
(2) Date: Jun. 13, 2014

(87) PCT Pub. No.: WO2013/093331
PCT Pub. Date: Jun. 27, 2013

(65) Prior Publication Data
US 2014/0318251 A1 Oct. 30, 2014

(30) Foreign Application Priority Data

Dec. 19, 2011 (FR) ...................................... 11 61915

(51) Int. Cl.
*G01N 29/07* (2006.01)

(52) U.S. Cl.
CPC ....... *G01N 29/07* (2013.01); *G01N 2291/011* (2013.01); *G01N 2291/0234* (2013.01);
(Continued)

(58) Field of Classification Search
CPC ............ G01N 29/07; G01N 2291/011; G01N 2291/02827; G01N 2291/265
(Continued)

(56) References Cited

U.S. PATENT DOCUMENTS

| 3,416,365 A | 12/1968 | Frederic |
| 5,447,069 A | 9/1995 | Johnson et al. |

(Continued)

FOREIGN PATENT DOCUMENTS

| JP | 2000-221076 | 8/2000 |
| JP | 2005-083797 | 3/2005 |

(Continued)

OTHER PUBLICATIONS

International Search Report Issued Apr. 17, 2013 in PCT/FR12/052980 Filed Dec. 19, 2012.

(Continued)

*Primary Examiner* — John Chapman, Jr.
(74) *Attorney, Agent, or Firm* — Oblon, McClelland, Maier & Neustadt, L.L.P.

(57) ABSTRACT

A method measuring elastic properties using ultrasound of a part made of a material having a curved surface, includes: emission of bundles of ultrasound waves in a direction of a point of impact on the part's surface to generate waves within the part; knowing a thickness d of the part at the point of impact in a first direction $D_1$ and a thickness d2 in a second direction forming an angle determined with respect to the first direction, taking a first measurement t1 of time taken by the longitudinal waves transmitted to travel d1 from the point of impact, and taking a second measurement t2 of the time taken by the transverse waves to travel d2 from the point of impact; and determining the Young's modulus and/or Poisson's ratio of the material based on the longitudinal velocity VL=d1/t1 and transverse velocity VT=d2/t.

5 Claims, 3 Drawing Sheets

(52) U.S. Cl.
CPC .............. *G01N 2291/02827* (2013.01); *G01N 2291/265* (2013.01); *G01N 2291/2634* (2013.01)

(58) Field of Classification Search
USPC .......................................................... 73/597
See application file for complete search history.

(56) References Cited

U.S. PATENT DOCUMENTS

| | | |
|---|---|---|
| 6,057,927 A | 5/2000 | Levesque et al. |
| 2002/0112540 A1 | 8/2002 | Zeroug et al. |

FOREIGN PATENT DOCUMENTS

| | | |
|---|---|---|
| JP | 2008 232825 | 10/2008 |
| WO | 99 44051 | 9/1999 |

OTHER PUBLICATIONS

Office Action issued Sep. 13, 2016 in Japanese Patent Application No. 2014-546620 (with English translation only).

METHOD FOR MEASURING ELASTIC PROPERTIES USING ULTRASOUND

TECHNICAL FIELD

The invention relates to a non-destructive test method and more particularly to a method for non-destructively determining, by ultrasound, the elastic properties of an isotropic metal material.

PRIOR ART

There is a permanent need for methods to be available that make it possible to determine the elastic properties, such as the Young's modulus or the Poisson's ratio, of parts made of homogeneous and isotropic materials. There is a particular need for a method relating to a part with curved external surfaces. Determining the Young's modulus using ultrasound waves is known for planar parts but for complex parts, where the external surfaces are curved, it is difficult to place the transmitters and receivers correctly in order to obtain reliable results.

A known means for calculating the longitudinal modulus of elasticity - the Young's modulus—of complex parts consists of producing dumbbell-shaped test pieces that are placed between the jaws of tensile testing machines. However, the production of dumbbell-shaped test pieces is not always possible or can be very expensive for some materials. In addition, the shape of the test piece is often very different from that of the part used. Depending on the method of manufacturing the parts, measuring their modulus of elasticity may not be relevant.

The present applicant has set itself the objective of perfecting a non-destructive method for examining complex parts, in particular complex parts with curved shapes, and proposes to use ultrasound waves to determine the elastic properties such as the longitudinal modulus of elasticity and the Poisson's ratio.

U.S. Pat. No. 3,416,265 describes a method for determining the elastic properties of a part having a curved surface and of a given thickness using the measurement of the longitudinal and transverse waves travelling through a material of which the thickness is known, however it does not teach its application to a part that has two thicknesses in different directions.

DISCLOSURE OF THE INVENTION

According to the invention, the method for determining the elastic properties of a part having a curved surface, comprising the emission of beams of ultrasound waves towards a point of impact on the surface of the part so as to generate the transmission of waves within said part, is characterised in that, knowing the thickness $d_1$ of the part at said point of impact in a first direction $D_1$ perpendicular to the tangent plane at that point and the thickness $d_2$ in a second direction $D_2$ forming an angle a determined with respect to the first direction,
- a measurement of the time $t_1$ taken by longitudinal waves transmitted to travel within the part the distance $d_1$ from said point of impact;
- a measurement of the time $t_2$ taken by transverse waves transmitted within the part to travel the distance $d_2$ from said point of impact;

are taken.

The Young's modulus and/or the Poisson's ratio of the material are determined on the basis of the longitudinal velocity $V_L = d_1/t_1$ and the transverse velocity $V_T = d_2/t_2$.

Preferably, the beam of ultrasound waves is emitted through a coupling fluid, such as water.

The method is applicable, advantageously, to a part made of an isotropic material.

More particularly, the method is applicable to a spherical part, $d_1$ corresponding to the diameter of the sphere and $d_2$ to the length of a chord forming said angle $\alpha$. For example, the method is advantageously applicable to the examination of metal balls, particularly metal balls made of stainless steel; it is also of particular value for balls made of a ceramic material such as $Si_3N_4$, SiC or $ZrO_2$, which are used in bearings. However, the method is not limited to a spherical part and can be applied to more complex shapes insofar as a model, in particular a computer model, is available that enables the path of the ultrasound waves inside the part to be predicted mathematically.

It will be recalled that waves transmitted in the part are defined in relation to the interface plane between the part and the external environment, which serves as a reference for identifying the polarisation of the transverse and longitudinal waves. These waves are polarised in the sagittal plane, perpendicular to the interface plane, the transverse waves being generated by the transmission of the longitudinal waves through the interface.

It is known that the elastic properties of a metal sample have an effect on the transmission of the longitudinal and transverse waves and on their velocity, which in turn makes it possible to calculate the elastic properties using the knowledge thereof. The mechanics of small deformations connects the velocity of propagation of the longitudinal waves $V_L$ and the velocity of propagation of the transverse waves $V_T$ to the Young's modulus E and the Poisson's ratio v.

The relationships are as follows:

$$E = \rho V_T^2 (3V_L^2 - 4V_T^2)/(V_L^2 - V_T^2)$$

$$v = 0.5(V_L^2 - 2V_T^2)/(V_L^2 - V_T^2)$$

Thus, having calculated the propagation velocities $V_L$ and $V_T$, parameters are available that enable the Young's modulus and Poisson's ratio to be calculated and on the basis of that, the other features of the material.

BRIEF DESCRIPTION OF THE FIGURES

The invention will be better understood, and its other aims, details, features and advantages will become more clearly apparent on reading the detailed explanatory description that follows, of embodiments of the invention given as purely illustrative and non-limiting examples, with reference to the appended diagrammatic drawings.

In these drawings

DETAILED DESCRIPTION OF THE INVENTION

To illustrate the invention, the method has been applied to the examination of a stainless steel sphere. In the example developed here, the sphere has the following features:
diameter=19.050 mm;
mass=28.1865 g;
density $\rho=7,789.2$ kg/m$^3$
Measurement of the velocity of propagation of the longitudinal wave A transducer 2 is plunged into a coupling fluid 3, which is water, with the sphere 1. The transducer, such as the Panametrics V322-6 10 MHz transducer with a focal length of 6 inches, is connected electrically to a workstation for controlling and for receiving signals, which is not shown. It is placed in transmit-receive mode and is oriented along the axis passing through the centre of the sphere.

Figure 1:
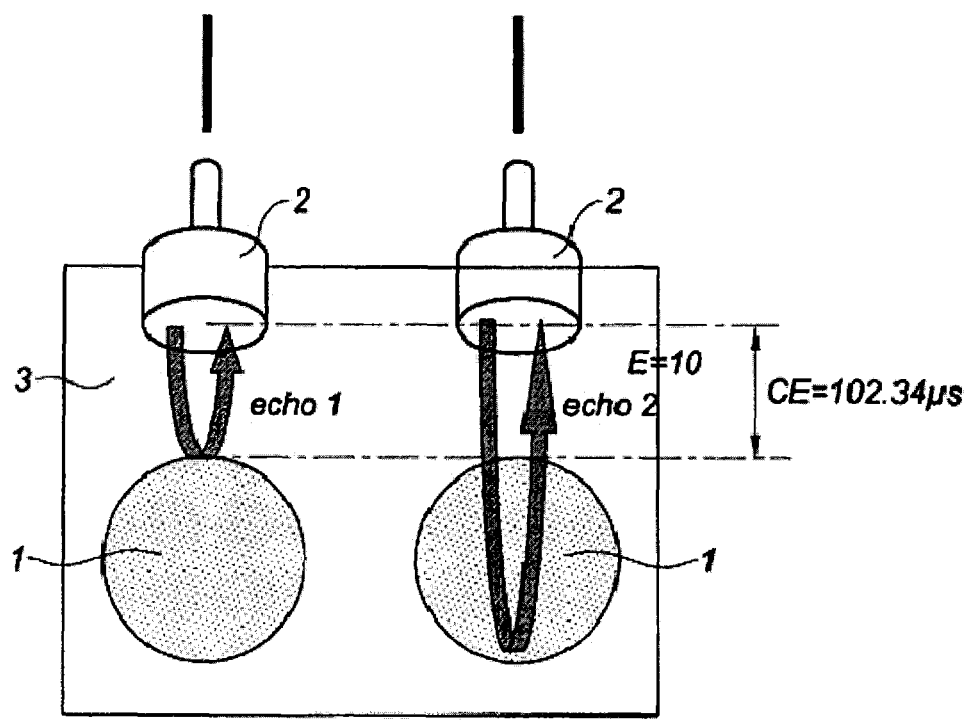
FIG. 1 is a diagrammatic illustration of the position in reflection mode of an ultrasound transducer relative to a sphere to be analysed and the two successive reflections of the longitudinal ultrasound wave on the sphere.
Figure 2:
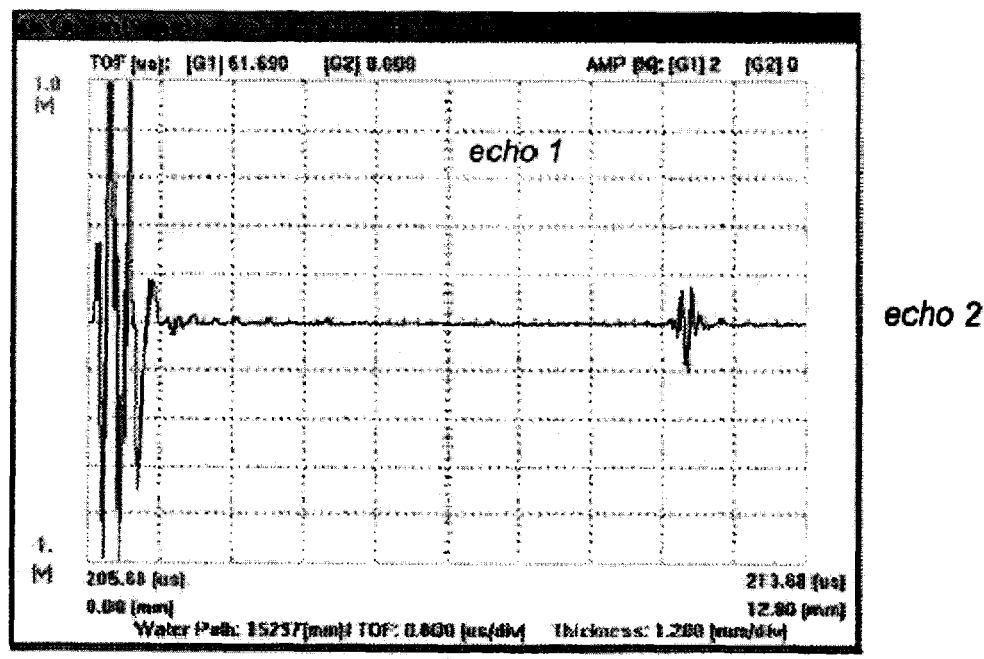
FIG. 2 shows the trace on an oscilloscope of the variation in the signal produced by the transducer in the case shown in FIG. 1 with the interface echo and the reflection on the bottom of the sphere.

From the graph of the amplitude of the ultrasound wave produced as a function of time, as shown in FIG. 2, the propagation time $t_{L1}$ of said wave is seen between the transducer 2 and the interface at the surface of the sphere on one side and the propagation time $t_{L2}$ between the transducer 2 and the bottom of the sphere seen from the transducer.

The propagation times identified on the graph in FIG. 2 are as follows:

$$t_{L1}=205.517 \ \mu s$$

$$t_{L2}=211.897 \ \mu s$$

The velocity of propagation of the longitudinal wave $V_L$ is therefore the ratio of twice the diameter of the sphere over the travel time:

$$V_L=2\times \text{diameter}/(t_{L1}-t_{L2})$$

which, in the example, is $$38.10\times 10^{-3}/6.380\times 10^{-6}=5,971.8 \ m/s.$$

Measurement of the velocity $V_T$ of the transverse wave

The principle used is that of the propagation of a transverse wave $V_T$ in a direction $D_2$ forming a given angle $\beta$ relative to the direction $D_1$ of the longitudinal transmission wave by mode conversion in accordance with the principles of the Snell-Descartes laws.

The correct angle of incidence $\theta$ producing the propagation of a transverse wave forming the angle $\beta$, and the travel time $t_2$ in the sphere for this transverse wave are determined. The angle chosen is 45°.

Figure 3:
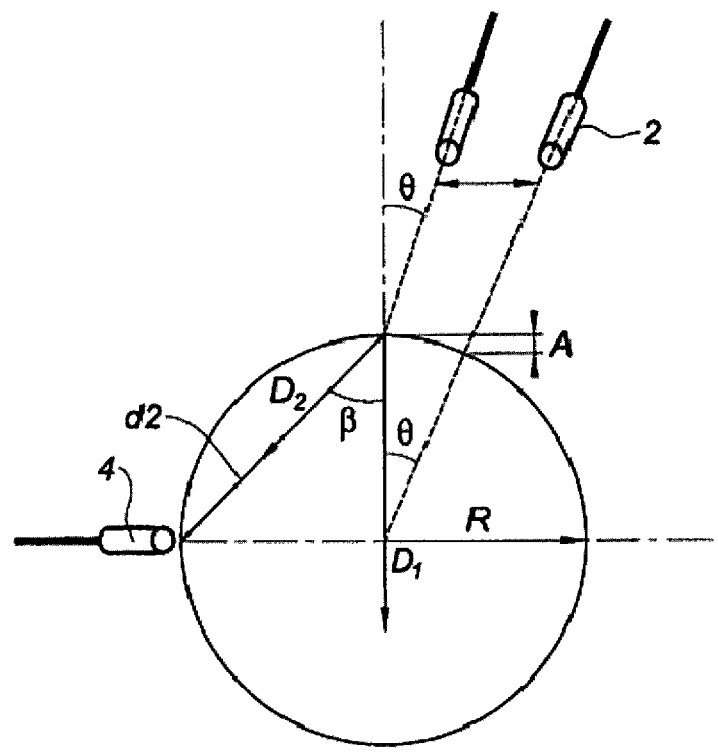
FIG. 3 is a diagram, not to scale, showing the two successive positions of an transmitting transducer for producing a transverse wave propagating at 45° towards a receiving transducer disposed laterally relative to the transmitter on the sphere.

The method is described with reference to FIG. 3; in this drawing, the sensors and the ball are not to scale, the ball is dilated relative to the sensors. For the measurement of $t_2$, separate measurements are taken of the transmission time $t_R$ of the waves through the coupling fluid and then of the transmission time $t_m$ in both the part and the coupling fluid, and the time $t_R$, where necessary corrected, is then subtracted from the time $t_m$.

The emitting transducer 2 is disposed in a coupling fluid with the sphere, a receiving transducer 4 like the transducer referenced I3-1004-R, 10 MHz 1" 0.25", is disposed laterally at the intersection of the direction $D_2$ with the sphere.

The velocity of propagation of the transverse wave is thus the ratio of the distance $d_2$ separating the point of impact of the ultrasound wave and the intersection with the sphere in this direction $D_2$: $d_2=R\times 2^{1/2}$ According to a first step, a measurement is taken of the precise travel time $t_R$ of the wave, for the given angle $\theta$, from the surface of the sensor to the normal to the sphere. The coupling fluid ensures that there is no superposition of echoes.

By placing the transducer in transmit-receive mode, the maximum amplitude of the reflected signal is determined. This maximum amplitude indicates that the signal is normal to the sphere at the angle $\theta$ concerned. As we are in transmit-receive mode, the travel time is half the time measured on the oscilloscope screen.

The sensor is then displaced horizontally, in such a way as to bring the beam to the top of the sphere. The displacement is calculated as a function of the radius R of the sphere $R\times tg\theta$ In this second step, the travel time $t_m$ of the wave to the receiving transducer 4 is measured.

The velocity of the transverse wave is the ratio of the distance $d_2$ travelled by that wave to the time $t_2$ taken to travel it. The measurement of the travel time has to be adjusted because of the fact that, as the transducer has been moved horizontally, the wave travels a shorter distance.

The adjustment of the path A in terms of time $t_A$ is expressed as follows:

$$t_A=R\times(1-\cos\theta)/\cos\theta\times V_{water}$$

where $V_{water}$ is the velocity of propagation in water.

As the measured time $t_m$ is the sum of the time $(t_R-t_A)$ corresponding to the path from the transducer to the surface of the sphere, and the time $t_2$ taken to travel along the length of the chord $d_2$, the travel time $t_2$ is therefore expressed as follows:

$$t_2=t_m-(t_R-t_A)$$

Figure 5:
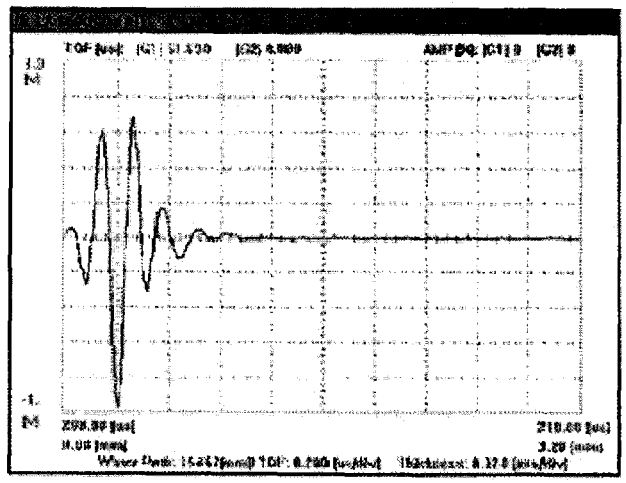
FIG. 5 is the illustration of the trace of the signal emitted by a transducer and reflected on the surface of the sphere.
Figure 6:
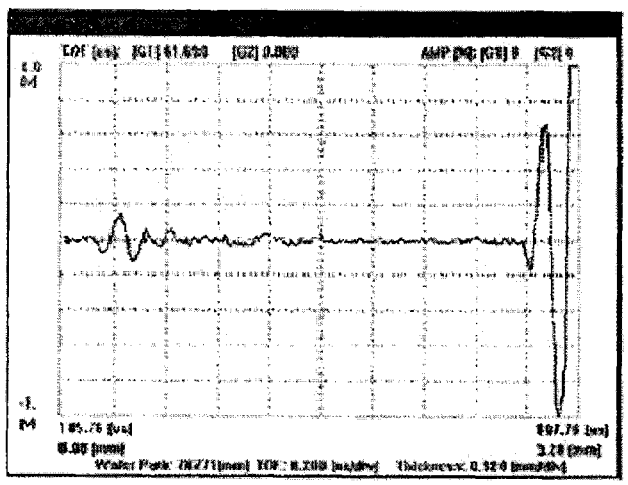
FIG. 6 is the illustration of the trace of the signal transmitted from the transmitting transducer to the receiving transducer.

The velocity of the transverse wave is the ratio of the path of travel $d_2=R\sqrt{2}$ to the time taken to travel this distance: $V_T=d_2/t_2$ For an angle $\theta$ of 19°, the following values are obtained (time measured with a digital oscilloscope accurate to 1 ns):
$V_{water}=1 \ 486.5$ m/s
$2\times t_R=202.63 \ \mu s$ (FIG. 5)
$t_m=105.02 \ \mu s$ (FIG. 6)
displacement: $R\times tg\theta=3.279$ mm
$t_A=R(1-\cos\theta)/\cos\theta\times V_{water}=0.3692 \ \mu s$
$d=\sqrt{2}\times R=13.470$ mm
$V_T=3 \ 306.2$ m/s The value 19° of the angle $\theta$ is an estimate. In order to obtain the correct value for the angle $\theta$, measurements are taken around this estimate. Thus, the operation above is repeated for values of the angle $\theta$ included in the range between 17° and 23°.

Figure 7:
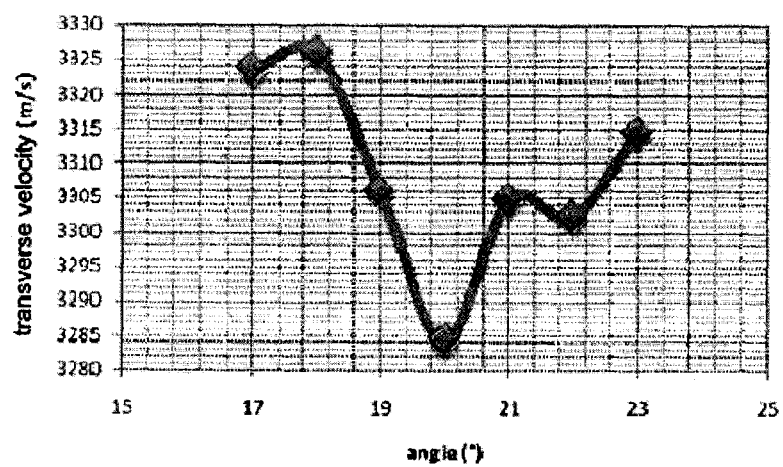
FIG. 7 shows the change in the calculated velocity of the transverse wave as a function of the angle of incidence.

The calculated velocity values are repeated
at 17° $V_T=3 \ 323.7$ m/s
at 18° $V_T=3 \ 326.1$ m/s
at 19° $V_T=3 \ 306.2$ m/s
at 20° $V_T=3 \ 284.4$ m/s
at 21° $V_T=3 \ 304.8$ m/s
at 22° $V_T=3 \ 302.3$ m/s
at 23° $V_T=3 \ 314.5$ m/s The curve obtained and reproduced in FIG. 7 has a point of minimum velocity; the velocity corresponding to the minimum point is associated with the shortest path of travel relative to the distance separating the two transducers.

Thus $V_T$=3 284.4 m/s

The values obtained for the transmission velocities of the sound wave make it possible to calculate the characteristic parameters of the part.

Calculation of the mechanical characteristics of a steel ball $\rho$=7 789.2 kg/m$^3$
$V_L$=5 971.8 m/s
$V_T$=3 284.4 m/s
$E=\rho V_T 2(3V_L^2-4V_T^2)/(V_L^2-V_T^2)$=215.6 GPa
$v=0.5(V_L^2-2V_T^2)/(V_L^2-V_T^2)$=0.283

Calculation of the mechanical characteristics of a ball made of silicon nitride $Si_3N_4$ $\rho$=3 166.5 kg/m$^3$
$V_L$=11 202 m/s
$V_T$=6 041.8 m/s
$E=\rho V_T 2(3V_L^2-4V_T^2)/(V_L^2-V_T^2)$=299.3 GPa
$v=0.5(V_L^2-2V_T^2)/(V_L^2-V_T^2)$=0.295

Figure 4:
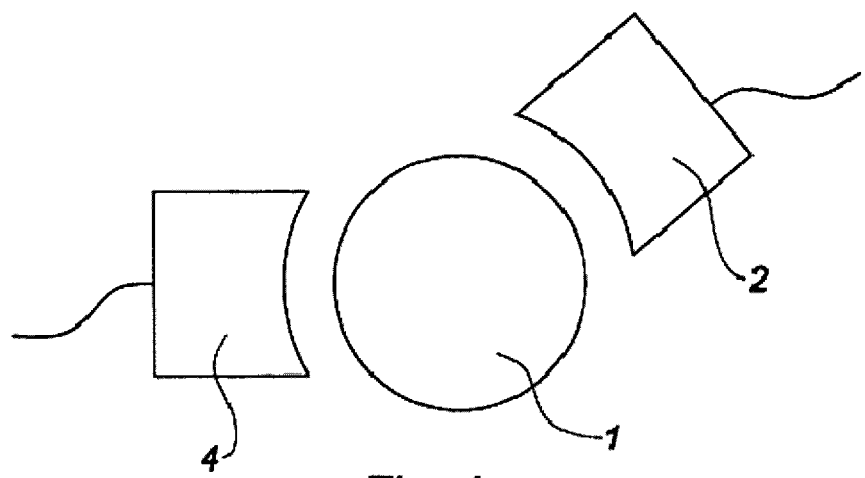
FIG. 4 shows an embodiment of the assembly using focused transmitting and receiving transducers.

It should be noted that to enable an accurate measurement to be taken, it is desirable to use a receiving transducer 4 with a very short focal length and therefore a small radius of curvature, which enables the ball to be centred, so that its axis coincides perfectly with the geometric axis of the transducer, the preferred configuration is shown in FIG. 4.

The invention claimed is:

1. A method for determining elastic properties of a spherical part, comprising;
    positioning an emitting transducer in a first position, the emitting transducer operating also as a receiver in said first position;
    emitting beams of ultrasound waves towards a point of impact on a surface of the spherical part so as to generate waves within the spherical part, the beams of ultrasound waves being emitted through a coupling fluid;
    determining a diameter $d_1$ of the spherical part at a first point of impact forming an angle of incidence $\theta$ with a first direction $D_1$ and a length of a cord $d_2$ in a second direction $D_2$ forming an angle $\beta$ with respect to the first direction $D_1$;
    providing a measurement of the transmission time $t_R$ of ultrasound waves to travel from the emitting transducer in said first position to the first point of impact;
    providing a first measurement $t_1$ of a time taken by longitudinal ultrasound waves transmitted to travel the distance $d_1$ the first point of impact based on the first position;
    displacing the emitting transducer to a second position with a second point of impact, in such a way to bring the beam to a top of the spherical part and to maintain the angle of incidence $\theta$ with the first direction $D_1$ producing waves forming the angle $\beta$ with the first direction $D_1$;
    providing a second measurement $t_2$ of the time taken by transverse ultrasound waves transmitted to travel the length of a cord $d_2$ from the second point of impact, given that for the measurement of $t_2$, the transmission time $t_R$ of the waves through the coupling fluid is corrected for displacement of the transducer to the second position, the transmission time $t_m$ in both the spherical part and the coupling fluid until a receiving transducer that is different from the said emitting transducer is measured, and the corrected time $t_R$ is then subtracted from the time $t_m$; and
    determining a Young's modulus and/or a Poisson's ratio of a material of the part based on a longitudinal velocity $V_L=d_1/t_1$ and a transverse velocity $V_L=d_2/t_2$.

2. The method according to claim 1, wherein the material of the part is isotropic.

3. The method according to claim 2, wherein the material is metal or ceramic.

4. The method according to claim 1, wherein the angle $\beta$ 45°.

5. The method according to claim 1, wherein the coupling fluid is water.

* * * * *

UNITED STATES PATENT AND TRADEMARK OFFICE
CERTIFICATE OF CORRECTION

PATENT NO. : 9,696,282 B2  
APPLICATION NO. : 14/365188  
DATED : July 4, 2017  
INVENTOR(S) : Jean-Yves Francois Roger Chatelier Page 1 of 1

It is certified that error appears in the above-identified patent and that said Letters Patent is hereby corrected as shown below:

In the Claims

Column 6, Line 9, change "distance $d_1$ the first" to --distance $d_1$ from the first--; and Column 6, Lines 37-38, change "angle β 45°" to --angle β is 45°--.

Signed and Sealed this  
Ninth Day of October, 2018

Andrei Iancu  
*Director of the United States Patent and Trademark Office*